United States Patent [19]

Vasquez et al.

[11] Patent Number: 4,670,245

[45] Date of Patent: Jun. 2, 1987

[54] DIAGNOSTIC PROCEDURES USING RADIOLABELED COLLOIDAL BISMUTH SUBCITRATE AND RELATED COMPOUNDS

[76] Inventors: Tony E. Vasquez, 5712 Verano, Irvine, Calif. 92715; Kenneth P. Lyons, 29 Cayuse La., Rancho Palos Verdes, Calif. 90274; Moussa Raiszadeh, 6760 Topaz St., Alta Loma, Calif. 91701; Manouchehre Fardi, 7886 Berner St., Long Beach, Calif. 90808

[21] Appl. No.: 604,870

[22] Filed: Apr. 27, 1984

[51] Int. Cl.$^4$ ........................ A61K 43/00; A61K 49/02
[52] U.S. Cl. .......................................... 424/1.1; 424/9
[58] Field of Search ...................................... 424/1.1, 9

[56] References Cited

U.S. PATENT DOCUMENTS 3,852,413 12/1974 Cammarata ........................... 424/1.1
4,115,540 9/1978 Digenis et al. ....................... 424/1.1
4,243,652 1/1981 Francis ................................. 424/1.1

*Primary Examiner*—Christine M. Nucker
*Attorney, Agent, or Firm*—Knobbe, Martens, Olson & Bear

[57] ABSTRACT

An unusual diagnostic procedure for the in vivo clinical evaluation of gastrointestinal ulcer disease and other diseases associated with loss of mucosal integrity in both animals and humans which comprises the oral administration of an effective amount of radiolabeled colloidal bismuth subcitrate or other ulcer avid bismuth compound to an animal or human host, followed by scintigraphic imaging of the gastrointestinal area of interest with scintigraphic imaging equipment. Also disclosed is a novel radiopharmaceutical composition comprising an aqueous solution or suspension containing an amount of a radiolabeled bismuth-protein complex effective for in vivo scintigraphic imaging of the gastrointestinal or other mucosal areas in animals and humans.

13 Claims, No Drawings

DIAGNOSTIC PROCEDURES USING RADIOLABELED COLLOIDAL BISMUTH SUBCITRATE AND RELATED COMPOUNDS

BACKGROUND OF THE INVENTION

This invention relates to a procedure and compounds for non-invasive imaging and diagnosis of upper gastrointestinal ulcers.

It is estimated that up to 10% of the population of the United States has upper gastrointestinal ulcer disease. Many of these patients will undergo either endoscopy or upper gastrointestinal X-ray examination. Additionally, many patients who do not have ulcer disease undergo these examinations in order to rule out such disease.

Upper gastrointestinal X-ray examination is currently the most common means for diagnosing ulcers. Images are taken after the patient swallows barium fluid. An ulcer will be revealed in profile as an indentation in the lining of the stomach or duodenum. However, failure to see an ulcer does not exclude it due to the high false negative rate for X-ray detection of duodenal ulcers. *Applied Radiology*, 20, 120 (May/June 1982).

One of the major drawbacks of X-ray/barium diagnostic techniques for upper gastrointestinal ulcers is the relatively poor resolution that can be obtained. Such X-ray techniques have about a 50% success rate in detecting 10 mm ulcers. In other words, smaller ulcers are virtually always missed in an X-ray diagnosis. However, as any gastroenterologist can certify, there is no rigid correlation between ulcer size and patient discomfort. The failure of X-ray techniques to visualize and diagnose relatively small ulcers is a serious drawback to that technique. Moreover, X-ray techniques necessarily entail exposure to a significant amount of ionizing radiation. The exposure problem is exacerbated by the fact that multiple exposures from different angles are required. The radiation exposure is typically 1000–2000 millirems/hr.

Endoscopy frequently reveals ulcers not seen by X-ray examination. Looking through a fiberoptic instrument, the physcian can light up the walls of the stomach and duodenum to visualize the ulcers. Endoscopy is associated with occasional complications. Sedation is required. The technique also entails the risk of serious complications such as perforation and aspiration. *Harrison's Principles of Internal Medicine* 1360 (9th ed. 1980).

Controlled clinical trials have shown that a derivative of colloidal bismuth subcitrate, tripotassium dicitrato bismuthate, marketed as a pharmaceutical in Europe under the trademark "De-Nol", healed duodenal and gastric ulcers significantly better than placebo. Several double-blind controlled clinical trials showed that tripotassium dicitrato bismuthate promoted ulcer healing in patients with chronic gastric or duodenal ulcers. *Gastroenterology* 82: 864–70 (1982).

We have developed a simple method for labeling colloidal bismuth subcitrate and related compounds with technetium-99m and other radioiostopes. The resulting solution is easily administered orally and imaging may be carried out with standard scintigraphic equipment. Animal studies show that the agent is stable in vivo and has utility for the clinical evaluation of gastrointestinal ulcer disease along with other diseases associated with a loss of mucosal integrity.

Accordingly, it is an object of the present invention to provide an alternative to X-ray/barium techniques and endoscopy for the diagnosis of upper GI ulcers and other disorders characterized by disruption of the gastrointestinal mucosa.

Another object of the present invention is to provide such a diagnostic technique that involves much lower exposure to ionizing radiation than does a complete X-ray series.

Still another object of the present invention is to provide a highly sensitive non-invasive diagnostic technique capable of detecting ulcers significantly smaller than can be resolved with x-ray techniques.

Still another object of the present invention is to provide a diagnostic technique for ulcers that requires relatively inexpensive equipment.

Yet another object of the present invention is to provide novel radiolabeled compounds for use in such a technique.

SUMMARY OF THE INVENTION

In furtherance of the foregoing objects, the present invention comprises an unusual diagnostic procedure for the in vivo clinical evaluation of gastrointestinal ulcer disease and other diseases associated with loss of mucosal integrity in both animals and humans which comprises the oral administration of an effective amount of radiolabeled colloidal bismuth subcitrate or related radiolabeled bismuth compound to a patient, followed by scintigraphic imaging of the gastrointestinal area of interest with scintigraphic imaging equipment.

The invention further comprises a complex of a radiolabeled protein with a colloidal bismuth salt wherein the radiolabel is one suitable for in vivo imaging of animals and humans.

The invention also comprises a lyophilized bismuth salt-tin protein complex in kit form which forms a bismuth-protein-radiolabel complex when rehydrated by adding a solution containing a medical radionuclide.

The invention still further comprises a novel radiopharmaceutical composition as an aqueous suspension or solution containing an amount of radiolabeled colloidal bismuth subcitrate or derivatives or precursors thereof effective for in vivo scintigraphic imaging of the gastrointestinal tract and other mucosal areas in humans.

Other objects, features and advantages of the present invention will become apparent from the following detailed description of the preferred embodiment which follows, when taken together with the accompanying examples.

DETAILED DESCRIPTION OF THE PREFERRED EMBODIMENTS

Colloidal bismuth subcitrate is a complex bismuth salt of citric acid. Quantitatively the composition is expressed in the formula:

$$Bi_x(OH)_y(C_6H_5O_7)_z$$

where the $C_6H_5O_7$ moiety represents citrate. When x is 1, y is $<3$, z is $\leq 3$, and y and z need not be integers. The trivalent $Bi(OH)_3$ and the trivalent citric acid have many possibilities for salt formation, and colloidal bismuth subcitrate comprises a mixture of many such complex salts.

In an acidic medium (pH$<5$), colloidal bismuth subcitrate precipitates. In all probability, bismuth-citrate bonds open, leading to the formation of various insoluble compounds, the smallest one being BiOCl; more complex structures containing free COO⁻ and Bi+ are also formed. Many, if not all, of these structures bind to proteins. This explains the observed formation of a diffuse precipitate on the gastric mucosa on the ulcer crater following administration of bismuth subcitrate. *Scandinavian Journal of Gastroenterology* 17 11–16, (Supp. 80 1982).

The mode of action of colloidal bismuth in the healing of ulcers is not fully understood. A number of derivative species are formed under acidic conditions. In the presence of hydrochloric acid, tripotassium dicitratobismuthate forms a precipitate containing bismuth oxychloride and bismuth citrate. It is believed to form protein-bismuth complexes in acid solution rather than simply neutralizing gastric acid. *Journal of Pathology* 139 105–114 (1983).

The technetium-99m labeled colloidal bismuth subcitrate of the present invention combines a short-lived radioisotope which is well-suited for diagnostic imaging with a new oral medication which selectively binds to ulcers in the stomach and upper small bowel. This provides a safe, non-invasive way to detect, localize, and evaluate the activity of ulcer disease in the upper GI tract, both for initial diagnosis and for follow-up re-evaluation.

The radiolabeled compounds of the present invention are formed by binding labeled protein to colloidal bismuth subcitrate or other bismuth salt. The protein is labeled with an appropriate medical radionuclide. Preferred labels are technetium-99m and iodine-123. Other gamma emitters, such as iodine-125, iodine-131, In-111, In-113m gallium-67 and bismuth radioisotopes may also be used; however, the compounds with a shorter half-life are preferred for obvious reasons. It is also possible to use a positron emitter, such as C-11, N-13, 0-15, gallium-68, or F-18 in place of a gamma emitter.

The first step in the synthesis of the novel radiolabeled compounds of the present invention is the formation of a radiolabeled protein. Although various proteins may be used, the preferred protein is human serum albumin. However, animal serum proteins may also be used to similar advantage. Suitable proteins include, for example, all of the globulins, such as gamma globulins, alpha globulins and beta globulins; globin; hemoglobin; ferritin; lactoferrin; transferrin; thrombin; fibrinogen; alpha lipoproteins; beta lipoproteins; plasminogen; ceruloplasmin; prothrombin; and ovalbumin, and may be from human, bovine, rabbit, or other animal sources. Proteins having a molecular weight over about 50,000 are preferred.

Although it is not possible to present an exhaustive catalog of suitable and unsuitable proteins, virtually all proteins, peptides, or amino acids which are suitable for oral administration and have suitable bonds or functional groups for attachment of the radiolabel can be used. (It will be understood that the term "protein" is used herein generically for such proteins, peptides, and amino acids.) For example, technetium-99m will bind to free carboxyl groups or hydroxy groups and iodine can be exchanged with hydrogen under a variety of conditions. Moreover, those of ordinary skill in the art will appreciate the ease with which potential proteins may be screened. Such a screening procedure would comprise combining the desired radioisotope with the protein as described below; combining the protein with the colloidal bismuth subcitrate, as is also described below; washing the resulting complex; and measuring the radiation level of the washed complex or of the eluant.

The bismuth compound of the present invention, preferably colloidal bismuth subcitrate, is dissolved in water or other suitable solvent. The pH of the solution, if needed, is then adjusted to between five and six using any suitable physiologically-acceptable acid or acid/base combination. The preferred combination is HCl and NaOH.

Human serum albumin, bovine albumin, or other suitable protein or peptide is dissolved in water. When, for example, the radioactive compound is Tc-99m, a reducing agent, such as stannous chloride, stannous fluoride, or stannous tartrate is then added to the protein solution to reduce the technetium from a +7 to a lower oxidation state, and the pH of the solution is adjusted to between about five and six. As will be apparent to those of skill in the art, compounds such as the radioactive iodine compounds must be oxidized (rather than reduced) before they can be incorporated into the protein. A suitable oxidizing agent, such as hydrogen peroxide, lactoperoxidase, or chloramin-T could be used.

The desired amount of radioactive material is added to the protein solution. In order to insure essentially complete binding of all radiolabel, it is best to use a large excess of protein; e.g., from $10^5$ to $10^6$ times more than a stoichiometric amount. The mixture is allowed to sit for between ten and thirty minutes at room temperature. The resulting solution is a radiolabeled protein solution.

The dissolved bismuth salt solution is then added to the labeled protein solution. The two solutions are gently mixed and allowed to stand at room temperature for between five and thirty minutes. The resulting solution is a bismuth-protein-radiolabel complex.

In an alternative synthesis, the protein is first added to the bismuth salt solution under acidic conditions to form a bismuth salt-protein complex. The necessary oxidizing or reducing agent (depending on the intended radiolabel) is added, together with a base or buffer (such as a phosphate or carbonate/bicarbonate buffer). The resulting solution may be labeled for immediate use, or may be lyophilized (freeze-dried) to form a bismuth-protein complex kit. The kit is rehydrated and labeled by adding a solution of radiolabel in an appropriate solvent, such as saline solution.

It should be understood that certain other bismuth compounds may be used in place of bismuth subcitrate to form a bismuth-protein-radiolabel complex that can bind to the proteins in disruptions of the gastrointestinal mucosa. Such compounds may be formed by using, in place of bismuth subcitrate, other bismuth salts such as bismuth subcitrate derivatives, such as the citrate salts, i.e., $Bi(C_6H_5O_7)_2^{-3}$, $Bi(C_6H_5O_7)$; the oxides, i.e., $Bi_2O_3$, $BiO^+$; the chlorides; i.e., $BiCl_3$, $BiCl_4^-$, $BiCl_2^+$, and other bismuth salts having an affinity for proteins, e.g., tripotassium dicitrato bismuthate, bismuth oxychloride, bismuth ammonium citrate, bismuth subcitrate-peptide complex, and bismuth gallate.

Because bismuth hydroxide is trivalent, it may bind to more than one protein. Accordingly, the labeled proteins are, in use, bound to the bismuth-citrate complex, which is in turn bound to the proteins in the ulcer crater. Accordingly, in preparing the compounds of the present invention, it is preferable to use a slight excess of bismuth complex in order to insure that the resulting complex contains reactive protein-affinitive sites.

The compounds are used by administering a desired amount and subsquently imaging the radiolabeled complex by suitable well-known techniques.

A suitable oral dosage for imaging purposes will ordinarily contain between about 1 and 10, and preferably between about 3 and 5 millicuries of radioactive label. It is best if the patient has been fasting for at least several hours prior to the test procedure.

After a suitable period, preferably between 0.5 and 2 hours after administration of the radiolabeled bismuth-protein complex residual unbound compound is flushed from the stomach and upper GI tract by administering a liquid to the patient. The radiolabeled compound binds to the site of the ulcer or other disruption of the mucosa and is imaged with suitable imaging machinery. The preferred imaging equipment is a gamma camera. A gamma camera is relatively inexpensive and is relatively portable. PET-scan equipment may be used if the labeling compound is a positron emitter. Other suitable imaging techniques will be apparent to those of skill in the art.

Imaging is preferably done between thirty minutes and five hours after administration of the compound. Best images are usually obtained between one hour and three hours after administration.

The following examples are presented solely to illustrate the invention and should not be regarded as limiting in any way.

EXAMPLE 1

1. 100-500 mg of colloidal bismuth subcitrate were dissolved in 0.5-1.0 ml of distilled water. The pH of the dissolved colloidal bismuth subcitrate was adjusted to pH 5-6 using NaOH/HCl.

2. To human serum albumin (5-10 mg) dissolved in 1 ml. of water, the required amount of stannous chloride (80-100 μg per kit) was added. The pH of the dissolved human serum albumin kit was adjusted to 3-6 with NaOH/HCl. Ten to twenty millicuries of technetium 99m pertechnetate were then added to the human serum albumin kit. The solution was allowed to stand at room temperature for twenty minutes.

3. The dissolved colloidal bismuth subcitrate (Step Number 1) was then added to the technetium 99m-labeled human serum albumin kit (Step Number 2). The combined solution was gently shaken and allowed to stand at room temperature for 15 minutes. More than 97% of the radiotracer was bound to the bismuth subcitrate-protein complex, and the radiolabel was stable for a minimum of 6 hours.

EXAMPLE 2

Gastric ulcers were induced in 3 adult 3 kg New Zealand rabbits by administering 600 mg/kg acetylsalicylic acid in 10 cc tap water. After four hours, 3-4 millicurie of the radiolabeled drug of Example 1 were orally administered in 5 cc of water. The rabbits were serially imaged with a gamma camera for the next 2 hours and the data were magnetically recorded. Specific areas of high scintigraphic activity were identified. Repeated imaging from different angles over a period of time was performed to identify areas of persistently increased activity.

The rabbits were then sacrificed and the stomachs were opened along the greater curvature, imaged, vigorously rewashed, and reimaged. Visual examination of the stomachs, both with and without the aid of a magnifying glass, revealed a one to one correspondence between actual ulcers and the imaged areas of increased activity. All 3 rabbits showed avid localized binding of radiotracer which remained fixed even with vigorous washing. Areas of normal appearing mucosa were relatively devoid of radiotracer. No false positives were obtained on rabbits without induced gastrointestinal ulceration. However, each visually-detected induced ulcer was also detected by the imaging technique, including ulcers as small as 0.5 mm.

Radiographic and chromatographic examination showed no significant radioactivity in thyroid, kidneys, liver, or bladder.

From our animal studies, we anticipate that studies with this agent will be significantly more sensitive for the detection and localization of upper gastrointestinal ulcer disease in humans than either of the two conventional techniques currently in use, i.e., upper gastrointestinal barium X-ray series and endoscopy. We have been able to clearly identify ulcers in our animal model.

Studies using radio-labeled colloidal bismuth subcitrate will cause only a minimal degree of discomfort. The total radiation exposure from this technique (based on a 3-5 millicurie dose) is no more than 60 millirems, or 5-10% of the dose from a conventional barium-upper GI X-ray series. Absorption of the compositions of the invention in the gut is virtually zero, and even repeated administration (e.g., 10 times) should involve no appreciable risk.

In comparison, conventional gastrointestinal barium X-ray series and endoscopy are associated with significant risk and often require the ability for agile cooperation on the part of patients.

Having fully described the invention, it is intended that it be limited only by the lawful scope of the appended claims and reasonable equivalents thereof.

What is claimed is:

1. A diagnostic procedure for the in vivo clinical evaluation of gastrointestinal ulcer disease and other diseases associated with loss of mucosal integrity, comprising:

orally administering an effective amount of a radiolabeled ulcer-avid bismuth-protein complex to a subject; and imaging the gastrointestinal area of the subject with scintigraphic imaging equipment.

2. The procedure of claim 1, further comprising the step of combining a bismuth compound or ion with a protein to form the bismuth-protein complex.

3. The procedure of claim 2, wherein the bismuth compound or ion is selected from the group consisting of colloidal bismuth subcitrate, $Bi(C_6H_5O_7)_2^{-3}$, $Bi(C_6H_5O_7)$, $Bi_2O_3$, $BiO^+$, $BiOCl$, $BiCl_3$, $BiCl_4^-$, $BiCl_2^+$, bismuth ammonium citrate, a bismuth subcitrate-peptide complex, and bismuth gallate.

4. The procedure of claim 2, further comprising the step of labeling said protein with a medical radionuclide.

5. The procedure of claim 1, wherein the complex is labeled with Technetium-99m or Iodine-123.

6. The procedure of claim 1, wherein the radiolabeled complex is prepared by combining colloidal bismuth subcitrate with radiolabeled protein under acidic conditions.

7. The procedure of claim 6, wherein the protein is albumin.

8. The procedure of claim 1 wherein the complex contains a colloidal bismuth salt.

9. Radiolabeled colloidal bismuth subcitrate.

10. A radiopharmaceutical composition, comprising a radiolabeled bismuth-protein complex.

11. The composition of claim 10, wherein the complex is formed of colloidal bismuth subcitrate and radiolabeled albumin.

12. A kit for making a radiolabeled bismuth-protein complex suitable for imaging ulcers and other conditions associated with loss of mucosal integrity in the upper gastrointestinal tract when orally administered to a patient, comprising a container of rehydratable lyopholized bismuth salt-protein complex, wherein said lyopholized complex, upon rehydration with a solution containing a medical radionuclide, becomes labeled with said radionuclide.

13. The kit of claim 12, wherein the bismuth salt is bismuth subcitrate.

* * * * *